United States Patent
Nair et al.

(10) Patent No.: US 6,361,785 B1
(45) Date of Patent: Mar. 26, 2002

(54) METHOD AND COMPOSITIONS FOR TREATMENT OF FUNGAL NAIL DISEASE

(75) Inventors: Muraleedharan G. Nair, Okemos; Russel S. Ramsewak; Sharon K. King, both of East Lansing; Manfred Stommel, Novi; Louise C. Selanders, East Lansing, all of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/655,561

(22) Filed: Sep. 6, 2000

Related U.S. Application Data

(62) Division of application No. 09/498,405, filed on Feb. 4, 2000.
(60) Provisional application No. 60/118,974, filed on Feb. 8, 1999.

(51) Int. Cl.[7] .................. A01N 25/34; A01N 65/00; A61K 35/78
(52) U.S. Cl. .................. 424/404; 424/725; 424/742
(58) Field of Search .................. 424/195.1, 401, 424/725, 742, 404; 514/728, 724, 772.6

(56) References Cited

U.S. PATENT DOCUMENTS 4,626,428 A * 12/1986 Weisberg et al. ............. 424/61
5,322,689 A * 6/1994 Hughes et al. ............. 424/401

OTHER PUBLICATIONS

Graedon et al. Vicks Vaporub Fights Nail Fungus; World Wide Web, www.bhip.com/people/22vicks.htm, 1999.*
Graedon et al. Vicks Vaporub Fights Nail Fungus, World Wide Web; http://www.bhip.com/people/22vicks.htm, accessed Jun. 17, 2000.*
Zaias, N., et al., J. Fam. Pract. 42 513–518 (1996).
Tom, C.M., et al., Am. J. Health–Syst. Pharm. 56 865–871 (1999).
Lugo–Somalinos, A., et al., J. Am. Acad. Dermatol. 26 408–410 (1992).
Einarson, et al., British Journal of Dermatology, 130 (Supplement 43), 32–34 (1994).
Doncker, Decrois, Pierard, Roeland, Woestenborghs, Jacomin, Odds, Heremans, Dockx & Roseeuw, Archives of Dematology 132(1), 34–41 (1996).
Roth, G.N., et al., J. Nat. Prod. 61 542–545 (1998).
Ramsewak, R.S., et al., J. Agric. Food Chem. 47 2, 444–447 (1999).

* cited by examiner

Primary Examiner—Jon P. Weber
Assistant Examiner—Patricia Patten
(74) Attorney, Agent, or Firm—Ian C. McLeod

(57) ABSTRACT

Compositions for the treatment of fungal nail disease (onychomycosis), including camphor, menthol, eucalyptus and thymol are described. The ingredients are natural and very effective in treating the nail fungus.

10 Claims, 6 Drawing Sheets

| Nail Assessment | | | | |
|---|---|---|---|---|
| Color (Infected toenail compared with healthy fingernail) | Normal<br>Slightly Yellowed<br>Very Yellowed<br>Dark Brown/Black | 0<br>1<br>2<br>3 | Right | Left |
| Thickness (in mm) | Normal<br>Slightly Thickened<br>Very Thickened<br>Very Thick & Crumbly | 0<br>1<br>2<br>3 | Right | Left |
| Separation from Nail Bed (in mm) | None<br>Slight<br>Moderate<br>Significant | 0<br>1<br>2<br>3 | Right | Left |
| Patient Reaction | | | | |
| Reported Change (Subjective judgement) | "Definitely better"<br>"May be better"<br>"No change"<br>"Worse" | 3<br>2<br>1<br>0 | Right | Left |
| Reported Pain (On scale of 0-10 where 0 = "Unbearable" and 10="None") | None<br>Slight, scale 3 or less<br>Moderate, scale 3-5<br>Significant, scale<5 | 3<br>2<br>1<br>0 | Right | Left |
| Frequency of Treatment (Number of treatments missed per month) | Used Daily<br>Missed<5/month<br>Missed>5/month<br>Hardly ever Used | 3<br>2<br>1<br>0 | Right | Left |

FIG. 5

EXTRACTION OF MEIJER'S VAPORUB
WITH ETHER AND METHANOL
a) ETHER:
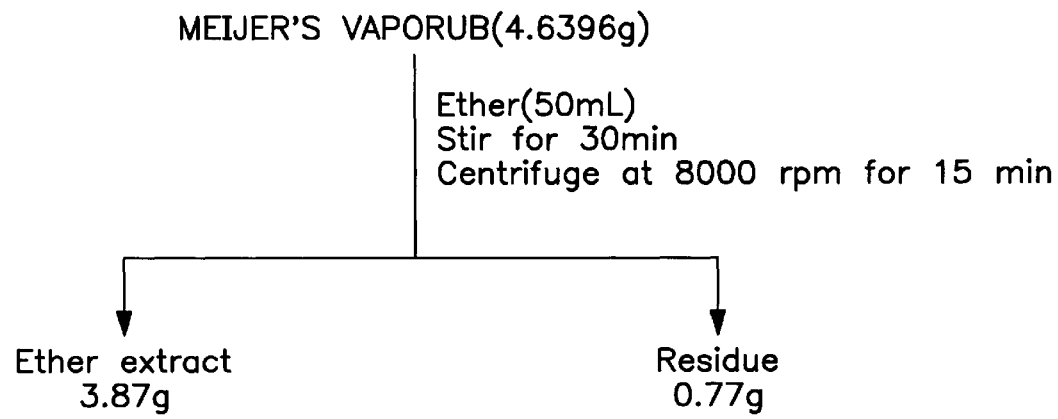
b) METHANOL:
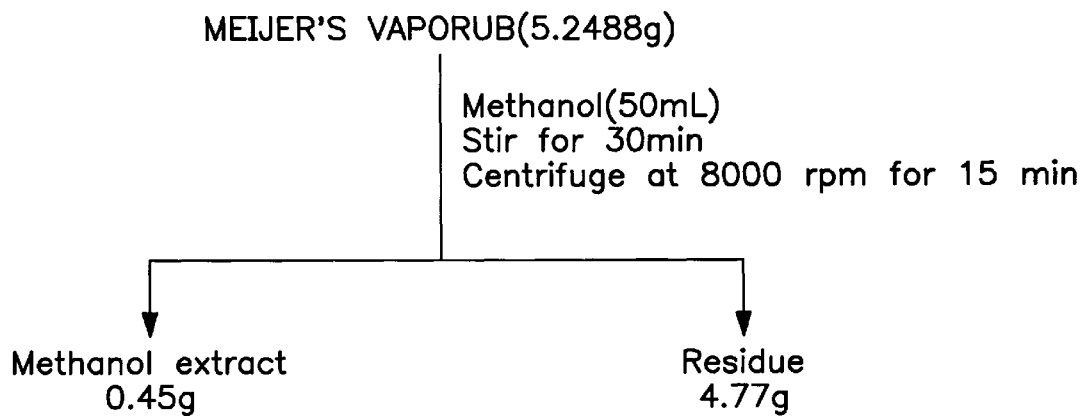
FIG. 6

METHOD AND COMPOSITIONS FOR TREATMENT OF FUNGAL NAIL DISEASE

This application is a divisional of application(s) application Ser. No. 09/498,405 filed on Feb. 4, 2000 and which designated the U.S.

BACKGROUND OF THE INVENTION (1) Field of the Invention

The present invention relates to novel topical compositions and method for the treatment of fungal nail disease. In particular, the present invention relates to the use of GRAS natural plant derivatives for this purpose.

(2) Description of Related Art

Fungal nail disease (onychomycosis) is the most commonly occurring nail disorder encountered in primary care. Current estimates indicate that nearly 11 million Americans are affected by fungal nail disease. It can affect toenails, fingernails or both and is usually caused by infectious organisms known as dermatophytes.

Fungal nail disease causes discoloration and thickening of the nail, accumulation of debris under the nail and, in severe cases, detachment of the nail plate from the nail bed. Toenails are the primary site of infection. Fungal nail disease can affect people of any age, gender and race and may cause discomfort and embarrassment due to the appearance of the nails.

Onychomycosis (tinea unguium) is defined as a localized infection of the nail or nail bed primarily caused by a pathogenic fungi; however, yeasts and molds can also cause infection. This disease is not life threatening, however, it can cause inconvenience, pain and discomfort to the individual and serve as a reservoir for infection. Infection can usually be determined by thickened, yellow or brown discolored, friable nail plates (Zaias, N., et al., J. Fam. Pract. 42 513–518 (1996)).

Onchyomycosis affects up to 30% of the population by age 60. The most common dermatophytes are Trichophyton rubrum and Trichophyton mentagrophytes (Zaias, N., et al., J. Fam. Pract. 42 513–518 (1996)). Although there are numerous topical agents on the market, none have been found to be satisfactory (Zaias & Serrano, Clinical Experimental Dermatology 14(2) 120–123 (1989)). Consequently, emphasis in research studies has focused on oral treatments.

Fungal infection of the fingernails or toenails are caused most commonly by dermatophytes (*Tricophyton rubrum, T. mentagrophytes, Microsporum canis, Epidermophyton Floccosum* and *E. stockdale*) which represent about 90% of the infection. Yeasts (*Candida albicans, C. parapsilosis.* and *C. krusei*) and nondermatophyte molds (*Scytalidium hyalinum, S. dimidiatum, Fusarium oxysporum, F. moniliforme, Acremonium chrysogenum, A. strictum, Aspergillus terreus, A. flavus,* and *Scopulariopsis brevicaulis*) are responsible for 7% and 3% of infections, respectively. These organisms infect the stratum corneum of the skin, hair and nails (Zaias, N., et al., J. Fam. Pract. 42 513–518 (1996); and Tom, C. M., et al., Am. J. Health-Syst. Pharm. 56 865–871 (1999)).

Immunodeficient patients, such as those with AIDS, the nail infection can be severe. Also, diabetics are known to be predisposed to certain cutaneous diseases but their frequency of infection is still not clear (Tom, C. M., et al., Am. J. Health-syst. Pharm. 56 865–871 (1999); and Lugo-Somalinos, A., et al., J. Am. Acad. Dermatol. 26 408–410 (1992)). There are four types of onychomycosis: (1) distal subungual onychomycosis (DSO) affecting the nail bed, (2) white superficial onychomycosis (WSO) affecting the surface of the nail plate, (3) proximal subungual onychomycosis (PSO) affecting the ventral and proximal area of the nail plate from the proximal nail fold, and (4) chronic mucocutaneous candidiasis (CMC) affecting the entire thickness of the nail plate (Zaias, N., et al., J. Fam. Pract. 42 513–518 (1996)).

DSO is the most common form and accounts for about 90% of the cases of onychomycosis. It is typically a lifelong infection and difficult to treat and is caused mainly by *T. rubrum*. A traumatized nail can become infected by species of Scytalidium or Scopulariopsis. WSO mainly involves the toenails and manifests itself as small, well-defined white spots on the surface of the nail plate. It is caused mainly by *T. mentagrophytes*. PSO accounts for less than 1% of the cases and is rare in healthy adults but occurs frequently in patients with AIDS. This type is caused by a preexisting *T. rubrum* that predates immunosuppression. CMC accounts for less than 1% of onychomycosis cases and invasion of the nail is by *C. albicans*. Most commonly, the organism originates in the intestinal tract and spreads from the mouth to the hand, eventually affecting the nail plate, nail bed and nail fold (Zaias, N., et al., J. Fam. Pract. 42 513–518 (1996); and Tom, C. M., et al., Am. J. Health-Syst. Pharm. 56 865–871 (1999)).

Onychomycosis never resolves spontaneously and recurrence after treatment is common. Treatment is difficult because of the unique properties of the nail unit. Thus, an effective antifungal agent must enter the affected tissue and persist there in high concentrations. The existing therapies must be continuous and used until the infected nail grows out and even after this lengthy treatment low cure rates and quick relapse times are common (Zaias, N., et al., J. Fam. Pract. 42 513–518 (1996); and Tom, C. M., et al., Am. J. Health-syst. Pharm. 56 865–871 (1999)). Treatments with topical creams are not as effective as oral treatments and prolonged periods of application are required. Griseofulvin, terbinafine and itraconazole are the drugs usually used for oral treatment.

Orally administered drugs that are available on the market also suffer from various drawbacks. Some are not very effective in controlling the fungal infection, some produce unwanted side effects, and all are quite expensive when compared to topical drugs. For example, Einarson, Aridian & Shear (Einarson, et al., British Journal of Dermatology, 130 (Supplement 43), 32–34 (1994)) studied the cost-effectiveness of griseofulvin (GRI), ketoconazole (KET) and terbinafine (TER). The expected treatment costs for toenail onychomycosis were $1049.77 for TER, $1388.54 for GRI and $1936.48 for KET. At the same time, success rates of the treatments were 78.3% for TER, 40.8% for KET and 17.5% for GRI.

A study by Korting, Schafer, Korting, Zienicke, Georgii & Ollert (Korting H., et al., Antimicrobial-Agents-Chemotherapy 37 (10) 2064–2068 (1993)) concurs that griseofulvin is minimally successful. In addition to unremarkable success rates and high costs, Zaias & Drachman (Zaias, N., et al., Journal of the American Academy of Dermatology 9(6), 912–919 (1983)) also report serious side effects with ketoconazole. Both griseofulvin and ketoconazole can cause elevated liver enzymes and ketoconazole has been shown to cause anti-androgenic dysfunction in males and adrenal dysfunction (Zaias & Serrano, Clinical Experimental Dermatology 14(2), 120–123 (1989)).

Recently itraconazole has been introduced as an effective oral treatment for onychomycosis. Its clinical cure rates are between 72% and 80% (Doncker, Decrois, Pierard, Roeland, Woestenborghs, Jacomin, Odds, Heremans, Dockx & Roseeuw, Archives of Dermatology 132(1), 34–41 (1996)). However, the cost of itraconazole is high and side effects include elevations of serum transaminases, alkaline phosphatase and bilirubin. Additionally, there are numerous drug interactions, including phenytoin, rifampin, Carbamazepine, isoniazid, cyclosporin, digoxin, terfenadine and warfarin (Nurses Drug Guide, 1996). Despite these known problems, many health care practitioners are currently prescribing pulse therapy with itraconazole, consisting of monthly one-week cycles of 400 mg daily for three to four months (Doncker, Van-Lint, Dockx & Roseeuw, Cutis 56(3), 180–183 (1995)).

In sum, because of the high cost and potentially dangerous side effects of oral antifungal agents, there are still no solutions for the treatment of onychomycosis using non-prescription products. Onychomycosis remains a concern for a large number of individuals. In light of these circumstances, an alternative topical agent that is inexpensive, and effective is needed.

OBJECTS

It is therefore an object of the present invention to provide topical compositions and a method for the use for treating fungal nail disease which produce very significant improvement. Further, it is an object of the present invention to provide compositions which use plant materials from natural sources which are GRAS General Recognized As Safe under U.S. regulations. Further still, it is an object of the present invention to provide compositions which are- inexpensive. These and other objects will become increasingly apparent by reference to the following description and the drawings.

SUMMARY OF THE INVENTION

The present invention relates to a method for inhibiting a dermatophyte in an infected nail in humans which comprises:

multiple separate applications of an effective amount of a composition which consists of an active ingredient selected from the group consisting of camphor, menthol, eucalyptus oil, thymol and mixtures thereof as active ingredients in a topical carrier to the nail until the dermatophyte is inhibited.

Further the present invention relates to a composition for treating a nail infection caused by a dermatophyte which consists essentially of:

(a) an effective amount of an active ingredient selected from the group consisting of camphor, menthol, eucalyptus oil, thymol and mixtures thereof; and (b) a topical carrier, wherein the active ingredient is present in an amount between about 0.01 and 25% by weight of the composition.

Further still, the present invention relates to a kit for the treatment of a nail infection caused by a dermatophyte which comprises:

(a) a closed openable container containing a composition which consists essentially of an effective amount of an active ingredient selected from the group consisting of camphor, menthol, eucalyptus oil, thymol and mixtures thereof in a topical carrier; and (b) application means for applying the composition on and under the nail which is infected with the dermatophyte.

The compositions can contain between 0.01 and 25% by weight of each of the ingredients based upon the weight of the composition. In a mixture of the four (4) ingredients the amount would be 100%. Preferably the amount is between about 1 and 10% by weight of each of the ingredients based upon the weight of the composition.

BRIEF DESCRIPTION OF THE DRAWINGS

FIG. 5 is a chart showing the assessment reading protocol for Example 2.

FIG. 6 is a chart showing the process for extracting a Vapo-rub (Meijer's brand, Michigan) with diethyl ether (VE) or methanol (VM) to remove the solid petroleum carrier.

DESCRIPTION OF PREFERRED EMBODIMENTS

Example 1

Antifungal, antimold, and antiyeast assay

Figure 1:
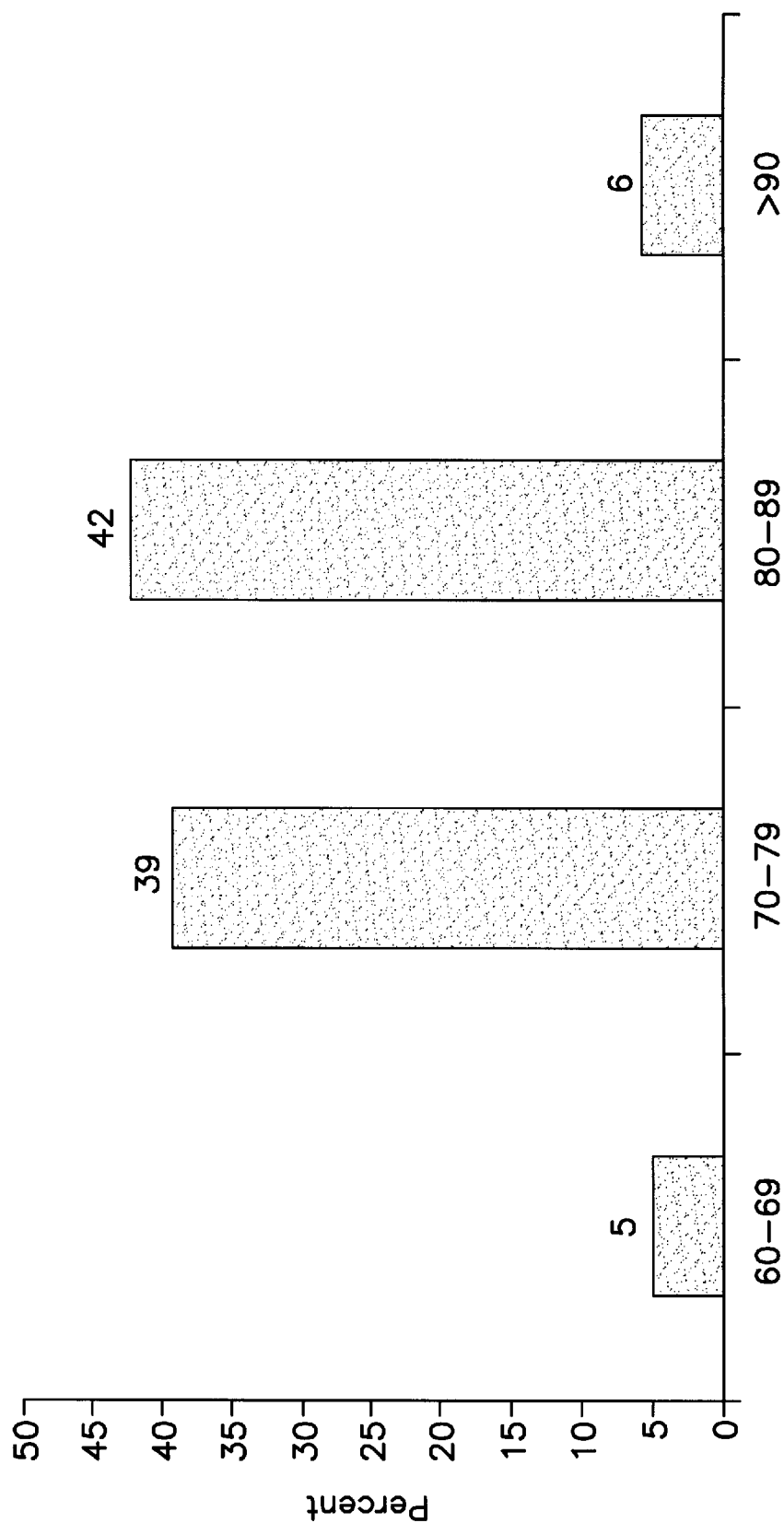
FIG. 1 is a bar graph showing the age of patients treated by compositions of the present invention.

*Tricophyton rubrum, T. mentagrophytes, Microsporum canis, Epidermophyton floccosum, Scytalidium hyalinum, S. dimidiatum, Fusarium oxysporum, F. proliferatum, Acremonium chrysogenum, A. strictum, Aspergillus terreus, A. flavus,* and *Scopulariopsis brevicaulis* used for the antifungal and antimold assays were cultured in Petri dishes containing PDA medium (20 mL). The test organisms *Candida albicans* (MSU strain), *C. krusei* (MSU strain), and *C. parapsilosis* (MSU strain) used for the antiyeast bioassays were cultured in Petri dishes containing YMG media (20 mL). The cells from a fully grown plate of each organism were suspended in saline solution (5 mL) and diluted to obtain $5 \times 10^4$ CFU/mL. 50 µL of this suspension were then used to inoculate agar plates (20 mL) or culture tubes containing the corresponding media (930 µL). Test compounds were dissolved in DMSO and added to the inoculated plates or tubes (20 µL) at concentrations ranging from 1000 to 0.1 µg/mL. The plates and tubes containing cell cultures and compounds were incubated at 27° C. for 72–96 hours. At the end of the incubation period, $MIC_{100}$ (the concentration of the test compound causing total inhibition of the test organism when compared to the control) for the test compounds were recorded for each test organism. Controls were prepared by adding DMSO (20 µL) to the inoculated tube or plate (Roth, G. N., et al., J Nat. Prod. 61 542–545 (1998); and Ramsewak, R. S., et al., J. Agric. Food Chem. 47 2, 444–447 (1999)). The results are shown in Tables 1 and 2.

TABLE 1

List of samples used for testing zones of inhibition.

| CODE | DESCRIPTION |
|------|-------------|
| C | DMSO Control |
| Ca | Camphor |
| M | Menthol |
| T | Thymol |

TABLE 1-continued

List of samples used for testing zones of inhibition.

| CODE | DESCRIPTION |
|---|---|
| 1 | *Cedrus atlantica* (Cedarwood Atlas) |
| 2 | *Cedrus deodora* (Cedarwood Himalayan) |
| 3 | *Juniperus virginiana* (Cedarwood Virginian) |
| 4 | *Eucalyptus citriodoa* |
| 5 | *Eucalyptus dives* (Eucalyptus Peppermint) |
| 6 | *Eucalyptus globulus* |
| 7 | *Eucalyptus radiata* |
| 8 | *Eucalyptus smithii* |
| 9 | *Eucalyptus staigeriana* |
| 10 | *Myristica fragrans* (Nutmeg) |
| 11 | *Pinus pinaster* (Turpentine) |
| VE | Meijer Vaporub - ether extract |
| VM | Meijer Vaporub - methanol extract |
| M1 | Mixture of Ca, M, T, and 1–11 (14 samples) |
| M2 | Mixture of Ca, M, T, and 4 (4 samples) |

TABLE 2

Zone of Inhibition (mm) for test samples after 7 days against organisms causing toe nail fingus at 250 µg/mL concentrations.
X denotes no observable zone of inhibition. VE, VM, M1 and M2 were tested at a higher concentration, 250 mg/mL.

| Organism | C | Ca | M | T | 1 | 2 | 3 | 4 | 5 | 6 | 7 | 8 | 9 | 10 | 11 | VE | VM | M1 | M2 |
|---|---|---|---|---|---|---|---|---|---|---|---|---|---|---|---|---|---|---|---|
| *Acremonium chrysogenum* | X | 10 | 15 | 20 | X | X | 7 | 14 | 9 | 13 | 11 | 14 | 8 | 6 | 5 | 7 | 14 | 37 | 37 |
| *A. strictum* | X | X | 9 | 12 | X | X | X | X | X | 7 | X | 8 | X | X | X | 3 | 4 | 12 | 25 |
| *Aspergillus flavus* | X | X | X | 6 | X | X | X | X | X | X | X | X | X | X | X | 5 | 7 | 10 | 20 |
| *A. terreus* | X | X | X | 3 | X | X | X | X | X | X | X | X | X | X | X | 3 | 3 | 7 | 15 |
| *Candida albicans* | X | 7 | 14 | 17 | X | X | X | 12 | X | 15 | 12 | 12 | X | X | X | 10 | 15 | 20 | 26 |
| *C. kruseii* | X | X | 12 | 16 | X | X | X | 9 | X | 8.5 | X | X | X | X | X | 3 | 10 | 11 | 16 |
| *C. parapsilosis* | X | 7 | 11 | 20 | X | X | X | X | X | X | X | X | X | X | X | 4 | 11 | 14 | 20 |
| *Epidermophyton floccosum* | X | X | 2 | X | X | X | 7.5 | 5 | 5 | 2 | X | X | 4 | X | 3 | 4 | 7 | 38 | 38 |
| *Fusarium oxysporum* | X | X | X | 2 | X | X | X | X | X | X | X | X | X | X | X | X | X | 10 | 20 |
| *F. proliferatum* | X | X | X | 3 | X | X | X | 4 | X | X | X | X | X | X | X | 3 | 5 | 12 | 20 |
| *Microsporum canis* | X | 2 | 3 | 20 | X | 9 | 6 | 11 | 7 | X | 6 | 9 | 13 | X | X | 2 | 4 | 38 | 38 |
| *Scopulariopsis brevicaulis* | X | X | X | 14 | X | X | X | X | X | X | X | X | X | X | X | X | X | 4 | 10 |
| *Scytalidium dimidiatum* | X | X | X | X | X | X | X | X | X | X | X | X | X | X | X | X | X | 10 | 15 |
| *S. hyalinum* | X | X | X | 5 | X | X | X | 1 | X | X | X | X | X | X | X | X | X | 12 | 14 |
| *Trichophyton mentagrophytes* | X | X | X | 10 | X | X | X | X | X | X | X | X | X | X | X | X | X | 38 | 38 |
| *T. rubrum* | X | 8 | 15 | 16 | X | X | X | X | X | X | X | 2 | X | X | X | X | 4 | 38 | 38 |

Example 2

The various test organisms were cultured in Petri dishes containing 20 mL of the respective medium (YMG, PDA, Malt Agar, or Sabouraud's agar). The cells from a fully grown plate of each organism were suspended in saline solution (5 mL) and diluted to obtain 5×10$^4$ CFU/mL. 1 µL of this suspension was then used to inoculate 24-well plates containing the corresponding media and agar (1 mL). Test compounds were dissolved in DMSO, acetone/EtOAc (1:1) or acetone/iso-amyl acetate (1:1) and added to the inoculated plates (20 µL) at concentrations ranging from 5000 to 1000 µg/mL incubated at 27° C. for 7 days. At the end of the incubation period, the MIC$_{100}$ (the concentration of the test compound causing total inhibition of the test organism when compared to the control) for the test compounds were recorded for each test organism. Controls were prepared by adding 20 µL DMSO, acetone/EtOAc (1:1) or acetone/iso-amyl acetate (1:1) to the inoculated plate.

Procedure 1 for MIC$_{100}$ Determination Using 24-Well Agar Plates at 1000 to 250 µg/ml of M2*.

The various test organisms are cultured in Petri dishes containing 20 mL of the respective medium (YMG, PDA, Malt Agar, or Sabouraud's agar).

The cells from a fully -grown plate of each organism are suspended in saline solution (5 mL) and diluted to obtain 5×10$^6$ CFU/mL.

50 µL of this suspension is then used to inoculate 24-well plates containing the corresponding media and agar (1 mL).

Test compounds are dissolved in DMSO, acetone/EtOAc (1:1) or acetone/iso-amyl acetate (1:1) and added to the inoculated plates (20 µL) at concentrations ranging from 1000 to 250 µg/mL incubated at 27° C. for 7 days.

At the end of the incubation period, the MIC$_{100}$ (the concentration of the test compound causing total inhibition of the test organism when compared to the control) for the test compounds are recorded for each test organism.

Controls were prepared by adding 20 µL DMSO, acetone/EtOAc (1:1) or acetone/iso-amy acetate (1:1) to the inoculated plate. *Mixture of Ca, M, T and Eucalyptus citriodora.

Procedure 2 for MIC$_{100}$ Determination using 24-Well Agar Plates—1000 to 125 µg/mL of M2.

The various test organisms are cultured in Petri dishes containing 20 mL of the respective medium (YMG PDA, Malt Agar, or Sabouraud's agar).

The cells from a fully grown plate of each organism are suspended in saline solution (5 mL) and diluted to obtain 5×10$^6$ CFU/mL.

1 µL of this suspension is then used to inoculate 24-well plates containing the corresponding media and agar (1 mL).

Test compounds are dissolved in DMSO, acetone/EtOAc (1:1) or acetone/iso-amyl acetate (1:1) and added to the inoculated plates (20 µL) at concentrations ranging from 1000 to 125 µg/mL incubated at 27° C. for 7 days.

At the end of the incubation period, the MIC$_{100}$ (the concentration of the test compound causing total inhibition of the test organism when compared to the control) for the test compounds are recorded for each test organism.

Controls were prepared by adding 20 µL DMSO, acetone/EtOAc (1:1) or acetone/iso-amyl acetate (1:1) to the inoculated plate.

Procedure 3 for MIC$_{100}$ Determination Using 24-Well Agar Plates at 5000–1000 µg/mL of M2.

The various test organisms are cultured in Petri dishes containing 20 mL of the respective medium (YMG, PDA, Malt Agar, or Sabouraud's agar).

The cells from a fully grown plate of each organism are suspended in saline solution (5 mL) and diluted to obtain 5×10$^6$ CFU/mL.

1 µL of this suspension is then used to inoculate 24-well plates containing the corresponding media and agar (1 mL).

Test compounds are dissolved in DMSO, acetone/EtOAc (1:1) or acetone/iso-amyl acetate (1:1) and added to the inoculated plates (20 μL) at concentrations ranging from 5000 to 1000 μg/mL incubated at 27° C. for 7 days.

At the end of the incubation period, the $MIC_{100}$ (the concentration of the test compound causing total inhibition of the test organism when compared to the control) for the test compounds are recorded for each test organism.

Controls were prepared by adding 20 μL DMSO, acetone/EtOAc (1:1) or acetone/iso-amyl acetate (1:1) to the inoculated plate.

The results are shown in Tables 3 and 4.

TABLE 3

List of samples used in $MIC_{100}$ determinations.

| CODE | DESCRIPTION |
|---|---|
| C | DMSO Control |
| A/E | Acetone/Ethyl acetate (1:1) |
| A/I | Acetone/Isopentyl (isoamyl acetate (1:1) |
| Ca | Camphor |
| M | Menthol |
| T | Thymol |
| 4 | *Eucalyptus citriodoa* |
| M2 | Mixture of Ca, M, T, and 4 (4 samples) in DMSO |
| M3 | Mixture of Ca, M, T, and 4 (4 samples) in A/E |
| M4 | Mixture of Ca, M, T, and 4 (4 samples) in A/I |

TABLE 4

$MIC_{100}$ (μg/mL) for mixtures M2, M3 and M4 against organisms causing toe nail fungus.

| Organism | M2 | M3 | M4 |
|---|---|---|---|
| Acremonium chrysogenum | 750 | 1000 | 1000 |
| A. strictum | 5000 | 5000 | 5000 |
| Aspergillus flavus | 5000 | 5000 | 5000 |
| A. terreus | 5000 | 5000 | 5000 |
| Candida albicans | 1000 | 2000 | 2000 |
| C. kruseii | 1000 | 2000 | 3000 |
| C. parapsilosis | 5000 | 5000 | 5000 |
| Epidermophyton floccosum | 2000 | 2000 | 2000 |
| Fusarium oxysporum | 3000 | 4000 | 4000 |
| F. proliferatum | 3000 | 4000 | 4000 |
| Microsporum canis | 750 | 2000 | 2000 |
| Scopulariopsis brevicaulis | 5000 | 5000 | 5000 |
| Scytalidium dimidiatum | 4000 | 5000 | 5000 |
| S. hyalinum | 5000 | 5000 | 5000 |
| Trichophyton mentagrophytes | 3000 | 4000 | 4000 |
| T. rubrum | 2000 | 3000 | 4000 |

Example 3

The solvents used in the present invention as the topical carrier are preferably esters of alcohols, such as isoamyl acetate. These carriers are used in nail polish remover, for instance, and provide a fruity smell to the composition.

The grease or jelly used in the Vapo Rubs available on the market are not essential and in fact are deleterious since they stain clothing. The topical carriers of the present invention are provided in solvents which evaporate or those which are absorbed into the skin and nails. All of this is well known to those skilled in the art.

Over the past decade, faculty in the College of Nursing at Michigan State University, East Lansing, Michigan have been involved in providing basic foot care services to elderly individuals in the community. During that time a multitude of individuals with varying levels of fungal nail involvement have sought foot care services. Initially, over-the-counter topical treatments were suggested as possible remedies. Patients often returned for subsequent foot care and reported that they had not carried through with treatment of over-the-counter anti-fungal medications because they could not see any improvement.

A "folk remedy" was reported to nurses by one of the individuals receiving foot care at the clinics. An elderly gentleman reported that he had totally cleared a bad case of toenail fungus in several months by daily applying VICKS® VAPO-RUB® (Procter & Gamble, Cincinnati, Ohio) to the affected nails. Subsequently, nurses suggested trying this treatment to several other patients at the foot clinics who had obvious toenail disfigurement due to fungal infection. VICKS® is comprised of the following as active ingredients:

Camphor
4.8%

Menthol
2.6%

Eucalyptus Oil 1.2%

Other ingredients are:

Cederleaf Oil, Nutmeg Oil, Special Petrolatum, Spirits of Turpentine, Thymol.

This original small group of individuals to whom VICKS® nail treatment was suggested was followed over the following months. The majority followed through with application of VICKS to their affected nail(s) on a regular or "almost always" basis. They were familiar and comfortable with the product and, at first, seemed amused that it might have a potential use beyond treating head and chest colds.

The nail changes that were observed were impressive. When individuals returned two months after they had begun applying VICKS® to fungal nails there was a clear line apparent on affected nails demarcating the presence of fungus from normal colored healthy nail. Over time, as nail growth continued, healthy nail replaced that which had been afflicted with a fungal infection. People continued daily application of VICKS® until all of the fungal nail had grown out and been replaced by healthy nail.

The treatment that was suggested to people with fungal infections of their toenail included massaging VICKS® into the nail once a day. Bedtime application, combined with wearing white cotton socks to bed to protect bed linens, was recommended. Orangewood sticks were provided so that persons who had the manual dexterity to do so could apply Vicks to the underside of the nail as well as the surface.

Charts were reviewed for 131 individuals who have attended the College of Nursing Foot Care clinics since 1995 when the use of VICKS® was first suggested as therapy for toenail fungus. Only active charts were reviewed, so this summary does not include the information from those persons which may have had Vicks recommended to them and subsequently expired or have been institutionalized. The college of Nursing foot care clinics are provided at local senior centers and, therefore, the majority of the persons taking advantage of these clinics are elderly.

Sociodemographics: Seventy percent of the people who have active charts at the foot clinics were female, a proportion that is consistent with the population demographics for persons in the age range who take advantage of the clinics. The majority of clients are quite elderly and range in age from 60 to 104. A Table 5 (see also FIG. 1) of the age range of clients follows:

TABLE 5

| Age Range | Percent of Total |
|---|---|
| 60–69 | 5% |
| 70–79 | 39% |
| 80–89 | 42% |
| >90 | 6% |

Figure 2:
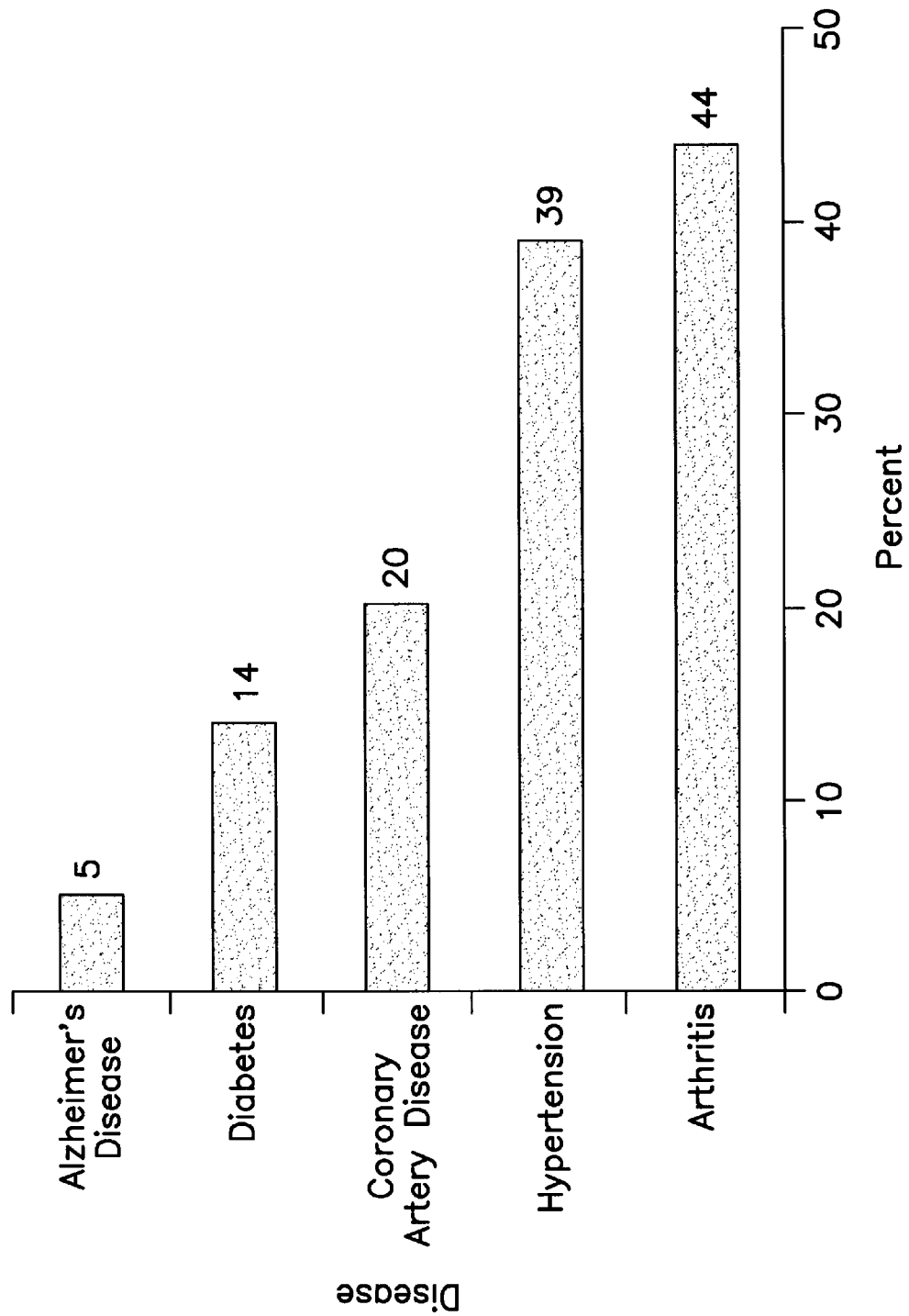
FIG. 2 is a bar graph showing the age and diseases of the patients of FIG. 1.

Additionally, information has been documented relating to the chronic diseases that clients at the foot clinics report. The following Table 6 (see also FIG. 2) indicates the incidence of the five most common chronic diseases reported by foot care clients.

TABLE 6

| Disease | Percent of Total |
|---|---|
| Arthritis | 44% |
| hypertension | 39% |
| Coronary Artery Disease | 20% |
| Diabetes | 14% |
| Alzheimer's Disease | 5% |

*It should be noted that percentages do not add up to 100% because some clients do report multiple chronic deseases.

*It should be noted that percentages do not add up to 100% because some clients do report multiple chronic diseases.

Figure 3:
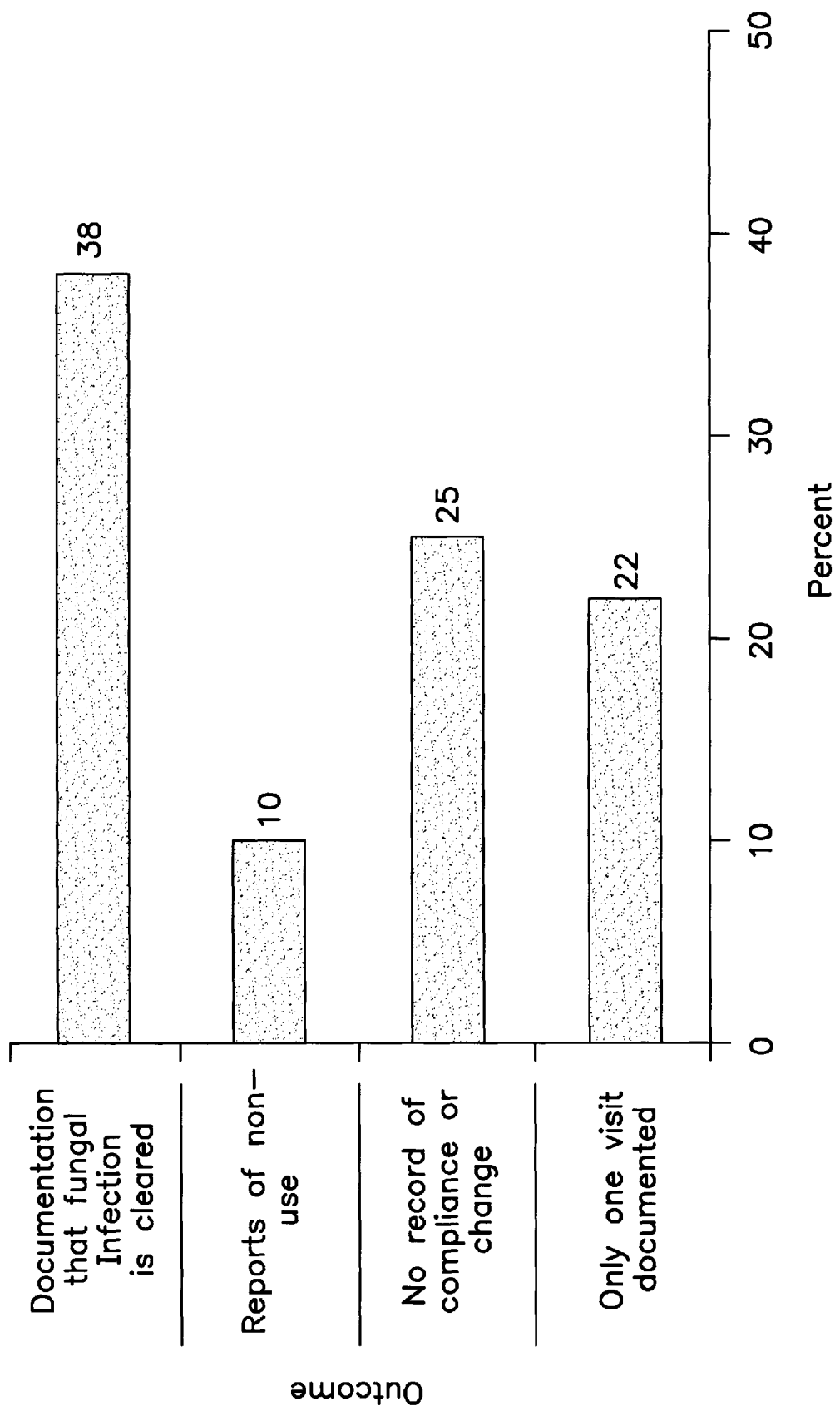
FIG. 3 is a bar graph showing the results with the patients of FIGS. 1 and 2.

Of the 131 active charts for our foot care clinics it has been documented that 85 of these persons (54%) presented with evidence of fungal toenails. VICKS® therapy was recommended for those 85 persons and the following outcomes were documented. It is important to keep in mind that these clinics have not been conducted for the purpose of research and that documentation has been considerably less than systematic relating to the outcomes resulting from prior recommendation of VICKS® for fungal infection therapy. The results are shown in Table 7 (FIG. 3).

TABLE 7

| Number, Percentage of Clients | Outcome |
|---|---|
| 19 (22%) | Only one visit documented |
| 21 (25%) | No record of compliance or change |
| 9 (10%) | Reports of non-use |
| 32 (38%) | Documentation that fungal infection is cleared |

The 25% of clients for whom no record of compliance or change are most probably the result of multiple clinicians at the foot care clinics and the fact that there was no intent, until recently, to document the outcome of VICKS® therapy. The reasons for non-use of recommended VICKS® therapy by clients include the following (1) wife objects to odor, (2) client cannot reach toes to apply VICKS®, and (3) client cannot remember to use.

Figure 4:
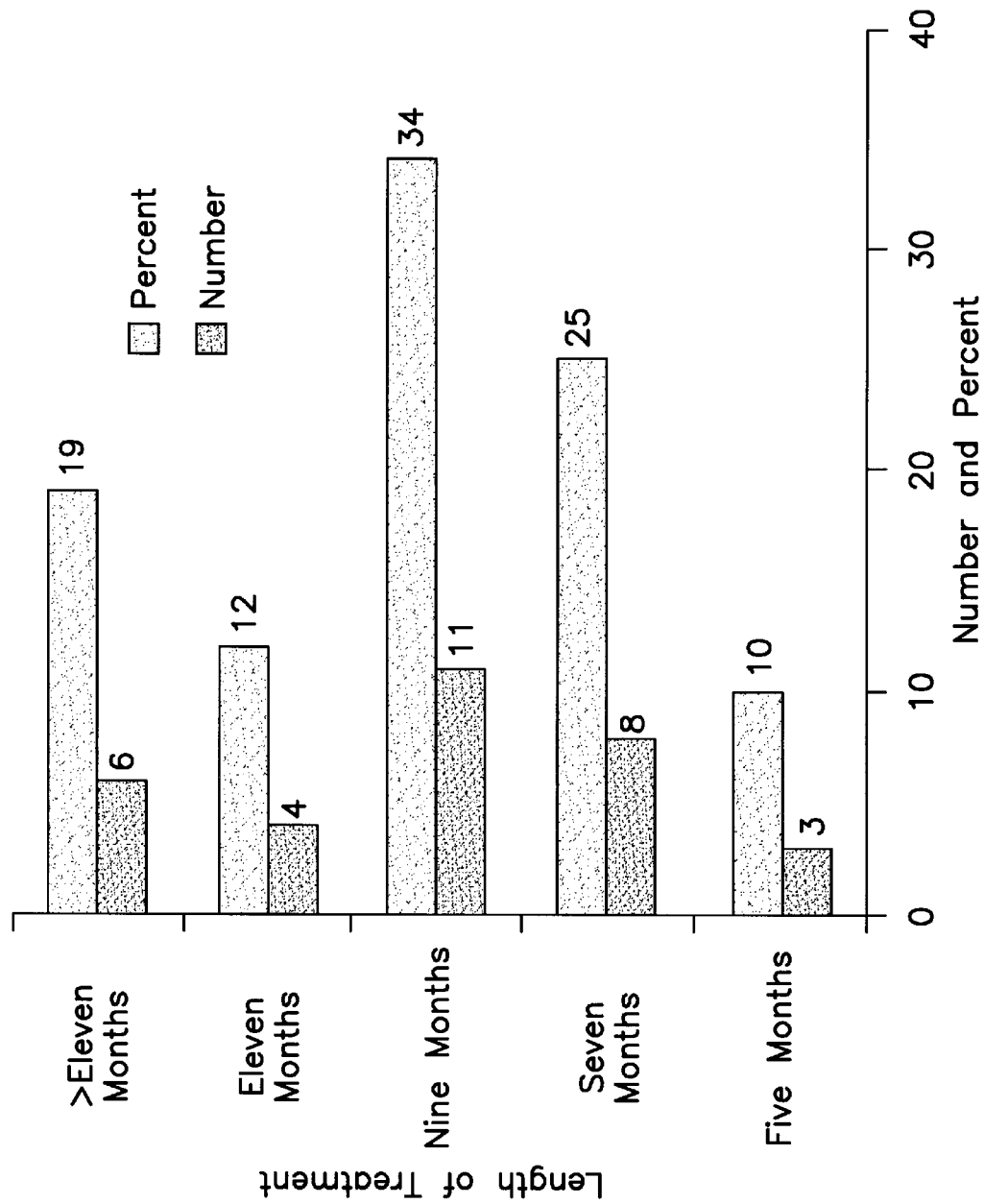
FIG. 4 is a bar graph showing the length of treatment of the patients.

For the 38% of clients for whom fungal infections of their toenails were cleared, the following Table 8 (FIG. 4) summarizes the length of time that it took before elimination of the infection occurred:

TABLE 8

| Length of Treatment | Number, Percentage |
|---|---|
| Five Months | 3 (10%) |
| Seven Months | 8 (25%) |

TABLE 8-continued

| Length of Treatment | Number, Percentage |
|---|---|
| Nine Months | 11 (34%) |
| Eleven Months | 4 (12%) |
| >Eleven Months | 6 (19%) |

The problem with VICKS® for use in treating nail infections is that the base is greasy, the active ingredients for fungal nail disease are unknown as are the necessary amounts. There are inactive ingredients in VICKS® which are unnecessary for the treatment of a nail infection caused by dermatophytes.

Example 4

The goal of this protocol is to vigorously test the effectiveness of the VICKS® treatment in reducing or eliminating toenail fungus. The protocol is also useful for treating the patients with the compositions of Examples 3 and 4. The basic study is a randomized control group design (Friedman, Furberg & DeMets, Fundamentals of Clinical Trials, 3rd ed. St. Louis, Mo: Mosby (1996)) with repeated measures of the outcomes. Eligible subjects who agree to participate are divided into three groups, defined by different levels of exposure to the intervention.

Group I receives VICKS® from the outset (after the intake assessment). Group 2 receives a placebo (of petroleum jelly) for the first month to be followed by two months of VICKS®, and group 3 receives two months of placebo treatment before VICKS® is employed during the last month. Starting at intake, subjects receive, at each monthly visit to the clinic, an unmarked, sealed, dark-colored, 1.5 ounce jar containing either Vicks Vapo-Rub or the placebo. The content of the jar is unknown to the patient and treating nurse. The intent of this "masking" (Meinert, C. L., Clinical Trials: Design, Conduct, and Analysis. New York, N.Y.: Oxford University Press (1986)) is primarily to convince patients to stick to the prescribed external applications. This is not an example of "complete masking" which would make the odor, quality and texture of the applications indistinguishable from each other. That is to say, patients will know when they are switched from petroleum jelly to VICKS®. But they do not know which application contains the effective ingredient. The sealed package also masks the identity of the intervention from the treating nurse creating a "double-blind" design. The purpose here is to minimize bias in measurement.

Subjects are randomly assigned to the three levels of the intervention using subject recruitment site as an additional blocking variable. (Site blocking is done to control for likely differences in subject composition by site.)

All measurement and assessments are conducted at intake and at three additional monthly follow-up meetings at the foot clinic. A total of 12 patient assessments ($A_{ij}$, wherein I=0, 1, 2, 3 refers to the intake and three follow-up assessments and j=1, 2, 3 refers to the three comparison groups) will be carried out. The combination of a between-group design and a repeated measures design allows for testing the effectiveness of the intervention through multiple, independent hypotheses.

For example, at time 1 after the first month of the intervention, group 1 should show a lower assessment means score (=a better toenail outcome) than the two placebo groups: $A_{11} < A_{12} = A_{13}$. At times 2 or 3, we would expect the following outcomes: $A_{21} < A_{22} <_{23}$ or $A_{31} < A_{32} < A_{33}$, since group 1 will consistently have longer exposure to VICKS® than group 2, and group 2 longer exposure than group 3. Another way of testing the effectiveness of the intervention is by means of within-group comparisons of the repeated measures, i.e., comparisons of assessment scores over time for a given group. Including the baseline pre-test at intake, there are four available measures for each individual. In group 1 where the effective intervention is started right away (time 0), we hypothesize the following: $A_{01} > A_{11} > A_{21} > A_{31}$; in group 2, effective intervention starts at time 2, so we hypothesize: $A_{02} = A_{12} > A_{22} > A_{32}$. By the same reasoning the hypothesis for group 3 is: $A_{02} = A_{12} = A_{22} > A_{32}$.

OUTCOME MEASURES

All measurements and assessments were conducted at intake and at three additional Assessment of progress towards normal toenails are accomplished by means of the "Structured Assessment Record Sheet" (see FIG. 5 for the instrument and the associate instructions for use). This measurement instrument has already been pretested on 14 patients who were independently assessed by a total of three nurses. With this instrument, patients' toenails are assessed on three dimensions: color, thickness and separation from the nail bed. Each toenail is rated separately on a rating scale ranging from 0 to 3. The resulting overall nail assessment score can range from zero (all ten toes of both feet are healthy) to 90 (10 toes×3 rating dimensions×individual maximum scores of 3). The distribution of actual scores in the small pilot sample of 28 assessments was as follows: 10.5 (means, 8.4 (standard deviation), 0–33 (range), 1.6 (skew). Eleven patients were assessed twice by independent nurse raters. The overall assessment scores from the independent raters correlated at a level of r=0.915 indicating that the administration of this assessment tool will result in a highly reliable measurement procedure.

In addition to the "objective" toenail assessment by the provider, patient reactions and experiences will also be recorded as well as their compliance with the therapeutic regimen. We expect "reported change" and "reported pain" to be correlated with the objective assessment. The additional subjective, ordinal compliance rating will yield a potential tool for comparing the compliance records of the three intervention groups.

SAMPLE SELECTION

A sample of 142 patients who have fungal infections of the toenail are recruited to take part in empiric testing of VICKS® as a treatment. Subjects are recruited from three sites outside of the area where previous foot care clinics have been conducted.

Subjects who are eligible to take part in testing meet the following criteria; (1) they have a fungal infection in at least one toenail, (2) they are not pregnant, (3) they are not minors, and (4) they are not taking oral anti-fungal medications and have not taken any such medications within the past three months.

Criteria for identification of fungal infection will include at least one of the following markers; (1) discoloration of the toenail as compared with the color of healthy fingernails, (2) thickening of the toenail, (3) crumbling of the toenail, and (4) accumulation of debris under the toenail.

SAMPLE SIZE

For optimal comparisons among the three intervention groups, the random assignment should yield comparison groups of equal size. Since some of the hypotheses involve between-group comparisons and others within group comparisons, required sample sizes vary depending on the test. The goal is to obtain data that result in statistically powerful tests of the main hypothesis that VICKS® has therapeutic effects in the treatment of toenail fungus. The first step in calculations of statistical power is to determine a meaningful "effect size" (Cohen, Jacob, Statistical Power Analysis for the Behavioral Sciences, 2nd ed. Hillsdale, N.J.: Lawrence Erlbaum Associates (1988), Lipsey, Mark W., Design Sensitivity: Statistical power for Experimental Research. Newbury Park, Calif.: Sage Publications (1990)) for our intervention.

A look at the assessment tool devised for this study reveals that the objective outcome scores are comprised of three subscales (measuring the three dimensions of color, thickness, and separation). On each dimension, the minimum score increment is 1. As one might expect, the scores on the assessment dimensions are positively correlated (®>0.5). This means that observable improvement in a single toenail is likely to result in a score increment of 3. This increment becomes our minimum (absolute) effect size by which we want the comparison groups to differ.

For statistical power calculations, we need an estimate of the standardized effect size which, for a three-way comparison, can be defined as $ES=\sigma_g/(\sigma_i+\sigma_g)$ wherein $\sigma_g$=the standard deviation of the comparison group means and $\sigma_i$ denotes the standards deviation of the remaining individual variation in the population. As can easily be seen, if the group means do not differ (=the null hypothesis of no effect) then both $\sigma_g$ and ES will be zero. If there is no individual within-group variation but each group mean differs from the others (=perfect effectiveness), then $\sigma_i$ will become zero and ES=1.

In order to translate the absolute effect size into the standardized effect size ES, we rely on Cohen's transformation: $ES=d/2\times(k+1)/(3(k-1))^{1/2}$, where d=the standardized difference between the highest and lowest group mean, and k=the number of comparison groups (Cohen, J., Statistical Power Analysis for the Behavioral Sciences. 2nd ed. Hillsdale, N.J.: Lawrence Erlbaum Associates (1988)). With three comparison groups, there are two group differences of 3 (as measured in actual outcome scores). Thus, if the two extreme groups in the population differ by more than a score of 6, our test should show a statistically significant finding.

To get the standardized effect, we divide the difference score by the estimated (from the pilot sample) within-group standard deviation of the scores. Thus d=2×3/8.4=0.714. With k=3, our estimate of the standardized effect size ES=0.292. In order to be able to discover a real effect size of this magnitude 90 percent of the time (=statistical power of 0.90) while maintaining a conventional significance level of 0.05, the required sample size is 49 subjects in each comparison group (see power tables on p. 314 in Cohen, 1988). It is important to note that these sample size projections are based on the hypotheses requiring the largest samples. The repeated measures comparisons of within-group changes over time require smaller samples (Lipsey, Mark W., Design Sensitivity: Statistical Power for Experimental Research. Newbury Park, Calif.: Sage Publications (1990)). In addition, gender blocking and covariate analysis (involving subject age, for instance) may further increase the statistical power of the proposed tests by reducing error variance.

In short, we believe that a sample size of 45 cases in each comparison group will constitute a powerful test of the main hypothesis with a greater than 90% probability that we will have a statistically significant finding when, in fact, Vicks Vapo-Rub has an effect.

PATIENT RECRUITMENT SITES AND RECRUITMENT TIME TABLE

Elderly patients are recruited from three sites. Sites are located in communities at least twenty miles from the places where prior foot care clinics have been held to avoid "contamination" related to earlier knowledge or experience with suggested treatment with Vicks. Each site has a foot care clinic that takes place once a month in the senior center of a small community. Individuals who take part in the foot care clinics were expected to range in age from 60 to 95 and, based on previous experience with foot care clinics, will probably be predominated by women. (60–70% of the individuals who attend current foot care clinics are female). Also based on prior experience, we expect over half of the persons who appear at the foot clinics to have fungal infections of their toenails. Each week, eighteen to twenty individuals are scheduled for foot care at each of the four-hour clinics.

The total observation period for the study was 12 months. Given an intervention and measurement period of 3 months, the phased recruitment period will be limited to a maximum of 9 months. In order to end up with a total of 135 subjects available for analysis (45 in each comparison group) and assuming a 5% non-compliance among subjects who initially agree to participate, 142. subjects must be enrolled (135/0.95=142) over the 9-month period. This is equivalent to 15 or 16 patients per month from all three sites combined.

The numbers in the following Table 9 provide an approximate estimate of the number of subjects that will be simultaneously enrolled in the study (see bottom line: monthly load). Built into the table is the assumption that 7 subjects (or 5%) will be lost due to attrition/non-compliance.

TABLE 9

Phased Enrollment and Observation of Subjects over 12 months.
Recruitment (italicized) and Observation Periods: Months since Intake of First Subject

| | 1 | 2 | 3 | 4 | 5 | 6 | 7 | 8 | 9 | 10 | 11 | 12 |
|---|---|---|---|---|---|---|---|---|---|---|---|---|
| | 15 | 15 | 15 | 15 | | | | | | | | |
| | | 16 | 15 | 15 | 15 | | | | | | | |
| | | | 16 | 15 | 15 | 15 | | | | | | |
| | | | | 16 | 15 | 15 | 15 | | | | | |
| | | | | | 16 | 15 | 15 | 15 | | | | |
| | | | | | | 16 | 15 | 15 | 15 | | | |
| | | | | | | | 16 | 15 | 15 | 15 | | |
| | | | | | | | | 16 | 15 | 15 | 15 | |
| | | | | | | | | | 15 | 15 | 15 | 15 |
| Monthly Load | 15 | 31 | 46 | 61 | 61 | 61 | 61 | 61 | 60 | 45 | 30 | 15 |

In order to maintain the stratification scheme by location site, monthly enrollment maintained a fixed proportion of cases from each of the three sites.

RECRUITMENT PROCEDURES

Individuals who attend the foot care clinics are screened for the presence of toenail fungus during the course of routine foot care. Those persons who do have fungal infections of their toenails are informed of the study and offered the opportunity to participate. It is explained that participation in the study involves daily use of a product that may or may not be effective in alleviating the fungal infection and restoring the toenail to a normal, healthy state. Subjects are assured that the products to be tested will not cause new damage to the nail and that they will receive the products free of charge.

Additionally, the subjects agree to refrain from the use of nail polish during the course of the study and to return to foot care clinics once a month for assessment of their feet. Routine foot care is provided monthly at no charge to the subject. All subjects in the three comparison groups will be provided with identical, written explanations of the study and will be given instructions for use of the product that has been provided to them. Each subject is asked to sign a consent form affirming that the study and the requirements of their participation was explained to them and that they had the opportunity to ask questions about the study. They are made aware that their participation is completely voluntary and that their decision to participate or not participate will in no way affect the availability of foot care services to them. They are assured that they may withdraw from the study at any time without penalty.

TRAINING OF NURSE DATA COLLECTORS

Data was collected by a team of four registered nurses who will conduct all of the foot care clinics. All nurses who participated in the study were trained in the provision of basic foot care and in the use of the assessment tool. Practice sessions were conducted with multiple raters rating the same patient's toenails. Results were compared and assessment instructions refined for maximum reliability. A written instruction sheet for use of the assessment tool was provided to each nurse on the foot care team.

PHASES OF RESEARCH

Phase 1:

During the first three months prior to data collection, the program: hired staff, complete arrangements at the three data collection sites, obtain final approval from institutional review boards, trained nurse interveners and data collectors and finalize intervention probes and instruments for data collection.

Phase 2:

During the second nine-month period, all 142 study subjects are recruited and intake assessments are conducted on all of them.

Phase 3:

This study phase concerns the data collection period for the outcome measures. It overlaps with Phase 2, but started one month after the enrollment of the first study subject and ends at the end of the 12th month when the last recruited subject completed the intervention and observation cycle of three months. During this phase, an approximate (depending on attrition) total of 420 patient assessments are processed at their monthly clinic visits.

Phase 4:

This final phase includes data analysis and the writing of the final report.

STATISTICAL ANALYSIS PLAN

As outlined in the Study Design Section, the goals of this research involved testing the effectiveness of the VICKS® treatment in reducing or eliminating toenail fungus. The study design is a randomized block design with repeated measures and the outcome measure approximates a continuous score variable. In sum, the resulting data is likely to meet the assumptions underlying multivariate analysis of variance or covariance models (Neter et al., Applied linear statistical models 2nd ed. Homewood, Ill.: RD Irwin (1985)). The specific hypotheses listed above was tested against the null-hypothesis that all group and time means ($A_{ij}$) will be equal.

SUPPLIES

A six month supply of Experimental and Control Products in unmarked, coded containers is obtained for each subject in the study. Because the study is conducted within the context of foot care clinics it was necessary to have foot care supplies in enough quantity to conduct four clinics each month over the course of a year. Paper supplies will be obtained to record assessments, provide information to subjects, record informed consent and maintain study records.

EQUIPMENT

A Polaroid® camera is used to photograph each subjects feet at intake and following treatment with Vicks Vapo-Ru. Photographs are maintained with the subjects records and provide visual evidence of changes in nail health.

The procedure set forth above provides a reliable basis for patient testing of all of the compositions of the present invention. Directions for "Structured Assessment Record Sheet" (FIG. 5).

Nail Assessment

* Color: Score from "0" for normal to "3" for dark brown/black for each toe. The total score for each foot will range from "0" to "15". Place the total score for each foot in the coding box for that foot.
* Thickness: Score from "0" for normal to "3" for very thick and crumbly for each toe. The total score for each foot will range from "0" to "15". Place the total score for each foot in he coding box for that foot.
* Separation from Nail Bed: Score from "0" for none to "3" for significant for each toe. The total score for each foot will range from "0" to "15". Place the total score for each foot in the coding box for that foot.

PATIENT REACTION

* reported Change: Score from "3" for definitely better to "0" for worse for each foot. The total score for each foot will range from "0" to "3" and should be recorded in the appropriate box for each foot.
* Reported Pain: Score from "3" for none to "0" for significant (<5 on a scale of 0–10 where 0="unbearable" and 10="none"). The total score for each foot will range from "0" to "3" and should be recorded in the appropriate box.
* Frequency of Treatment: Score from "3" for treatment used daily to "0" for treatment hardly ever used. The total score for each foot will range from "0" to "3" and should be recorded for each foot in the appropriate box.

It is intended that the foregoing description be only illustrative of the present invention and that the present invention be limited only by the hereinafter appended claims.

We claim:

1. A composition for inhibiting dermatophytes in an infected nail in humans which consists of camphor, menthol, eucalyptus oil, and thymol in a topical carrier which is absorbed by the nail and skin and is not a grease or jelly, wherein the composition has a minimum inhibitory concentration ($MIC_{100}$) of at least 750 μg/ml of the topical carrier against Acremonium chrysogenum, A. strictum, Aspergillus flavus, *A. terreus, Candida albicans, C. kruseii, C. parapsilosis, Epidermophyton floccosum, Fulsarium oxysporum, F. proliferatum, Microsporum canis, Scopulariopsis brevicaulis, Scytalidium dimidiatum, S. hyalinum, Trichophyton mentagrophytes*, and *T. rubrum*.

2. The composition of claim 1 wherein the eucalyptus oil is from *Eucalyptus citriodora*.

3. The composition of claim 1 wherein the carrier is selected from the group consisting of dimethyl sulfoxide, isoamyl acetate, acetone, ethyl acetate, and mixtures thereof.

4. The composition of claim 1 wherein the carrier is an ester of an alcohol.

5. A kit for the treatment of a nail infection caused by a dermatophyte which comprises:

(a) a closed openable container containing a composition which consists of an effective amount of a mixture of camphor, menthol, eucalyptus oil and thymol in a topical carrier for the mixture, wherein the carrier is absorbed by the nail and skin and is not a grease or jelly, and wherein the dermatophytes which are inhibited by the composition are *Acremonium chrysogenum, A. strictum, Aspergillus flavus, A. terreus, Candida albicans, C. kruseii, C. parapsilosis, Epidermophyton floccosum, Fulsarium oxysporum, F. proliferatum, Microsporum canis, Scopulariopsis brevicaulis, Scytalidium dimidiatum, S. hyalinum, Trichophyton mentagrophytes*, and *T. rubrum*; and (b) an applicator for applying the composition on and under the nail which is infected with the dermatophyte.

6. The kit of claim 5 wherein the composition contains a combined amount of between 0.01 and 25% by weight of the active ingredients in the topical carrier.

7. The kit of claim 5 wherein the carrier is selected from the group consisting of dimethyl sulfoxide, isoamyl acetate, acetone, ethyl acetate, and mixtures thereof.

8. The kit of claim 6 wherein the eucalyptus oil is from *Eucalyptus citriodora*.

9. The kit of claim 5 wherein the applicator is a stick.

10. The kit of claim 5 wherein the solvent is an ester of an alcohol.

* * * * *

UNITED STATES PATENT AND TRADEMARK OFFICE
CERTIFICATE OF CORRECTION

PATENT NO. : 6,361,785 B1
DATED : March 26, 2002
INVENTOR(S) : Muraleedharan G. Nair et al.

It is certified that error appears in the above-identified patent and that said Letters Patent is hereby corrected as shown below:

Column 1,
Line 38, "Onchyomycosis" should be -- Onychomycosis --.

Column 5,
Line 9, "citriodoa" should be -- citriodora --.

Column 6,
Line 11, "iso-amy" should be -- iso-amyl --.

Column 7,
Line 22, "citriodoa" should be -- citriodora --.

Column 10,
Line 69, "$A_{21} < A_{22} <_{23}$" should be -- $A_{21} < A_{22} < A_{23}$ --.

Column 13,
Table 9, first number on each line of Table should be italicized, except for "Monthly Load".

Column 16,
Line 49, "of Claim 6" should be -- of Claim 5 --.

Signed and Sealed this

Nineteenth Day of August, 2003

JAMES E. ROGAN
*Director of the United States Patent and Trademark Office*